United States Patent [19]

Shau et al.

[11] Patent Number: 5,610,286
[45] Date of Patent: Mar. 11, 1997

[54] DNA'S ENCODING NATURAL KILLER CELL ENHANCING FACTOR

[75] Inventors: Hungyi Shau, Cerritos; Sidney H. Golub, Los Angeles, both of Calif.

[73] Assignee: The Regents Of The University Of California, Oakland, Calif.

[21] Appl. No.: 299,162

[22] Filed: Aug. 31, 1994

Related U.S. Application Data

[63] Continuation-in-part of Ser. No. 232,189, May 3, 1994, abandoned, which is a continuation-in-part of Ser. No. 787,148, Nov. 4, 1991, Pat. No. 5,250,295.

[51] Int. Cl.⁶ .................................................. C12N 15/12
[52] U.S. Cl. ........................ 536/23.5; 530/380; 435/69.6
[58] Field of Search ............................... 536/23.1, 23.5; 530/380; 435/69.6

[56] References Cited

PUBLICATIONS

Shau et al. (1994, Jun.) Immunogenetics vol. 40, pp. 129–134.
Prosperi et al. (1993) J of Biol. Chem. vol. 268, No. 15 pp. 11050–11056.

*Primary Examiner*—John Ulm
*Assistant Examiner*—Prema Mertz
*Attorney, Agent, or Firm*—Poms, Smith, Lande & Rose

[57] ABSTRACT

Recombinant DNA molecules comprising a DNA sequence encoding either NKEF (Natural Killer Enhancing Factor) A or B or their amino acid sequence variants. Essentially pure natural killer enhancing factor comprising the amino acid sequence of NKEF A or B or their amino acid sequence variants. Compositions of matter for use in enhancing the activity of natural killer cells; the composition comprising an anchor moiety to which is linked either NKEF A or B or their amino acid sequence variants. Methods for enhancing the in vivo activity of natural killer cells; the methods comprising introducing in vivo a sufficient amount of either NKEF A or B or their amino acid sequence variants linked to an anchor moiety. In a method for inducing leukocyte activation and proliferation wherein the leukocytes are treated with a cytokine the improvement comprising treating the leukocytes with the cytokine in the presence of NKEF A or B or their amino acid sequence variants.

2 Claims, 3 Drawing Sheets

```
         B       CTGGAGTGAGGCCCTCGGATCGGCCCCGCCGGGGTCGGCCCACGGCCCTGGCGGAGC    57
NKEF A CCGTCTTGTTCTTGCCTGGTGTCGGTGGTTAGTTTCTGCGACTTGTGTTGGGACTGCTGA    60
NKEF B GCTGAGAACGCGGGTCCACGCGTGTGATCGTCCGTGCGTCTAGCCTTTGCCCACGCAGCT   117

A TAGGAAGATGTCTTCAGGAAATGCTAAAATTGGGCACCCTGCCCCCAACTTCAAAGCCAC   120
     B TTCAGTCATGGCCTCCGGTAACGCGCGCATCGGAAAGCCAGCCCCTGACTTCAAGGCCAC   177

A AGCTGTTATGCCAGATGGTCAGTTTAAAGATATCAGCCTGTCTGACTACAAAGGAAAATA   180
     B AGCGG...TGGTTGATGGCGCCTTCAAAGAGGTGAAGCTGTCGGACTACAAAGGGAAGTA   234

A TGTTGTGTTCTTCTTTTACCCTCTTGACTTCACCTTTGTGTGCCCCACGGAGATCATTGC   240
     B CGTGGTCCTCTTTTTCTACCCTCTGGACTTCACTTTTGTGTGCCCCACCGAGATCATCGC   294

A TTTCAGTGATAGGGCAGAAGAATTTAAGAAACTCAACTGCCAAGTGATTGGTGCTTCTGT   300
     B GTTCAGCAACCGTGCAGAGGACTTCCGCAAGCTGGGCTGTGAAGTGCTGGGCGTCTCGGT   354

A GGATTCTCACTTCTGTCATCTAGCATGGGTCAATACACCTAAGAAACAAGGAGGACTGGG   360
     B GGACTCTCAGTTCAACCACCTGGCTTGGATCAACACCCCCGGAAAGAGGGAGGATTGGG   414

A ACCCATGAACATTCCTTTGGTATCAGACCCGAAGCGCACCATTGCTCAGGATTATGGGGT   420
     B GCCCCTGAACATCCCCCTGCTTGGTGACGTGACCAGACGCTTGTCTGAGGATTACGGCGT   474

A CTTAAAGGCTGATGAAGGCATCTCGTTCAGGGGCCTTTTTATCATTGATGATAAGGGTAT   480
     B GCTGAAAACAGATGAGGGCATTGCCTACAGGGGCCTCTTTATCATCGATGGCAAGGGTGT   534

A TCTTCGGCAGATCACTGTAAATGACCCTCCCTGTTGCCGCTCTGTGGATGAGACTTTGAG   540
     B CCTTCGCCAGATCACTGTTAATGATTTGCCTGTGGGACGCTCCGTGGATGAGGCTCTGCG   594

A ACTAGTTCAGGCCTTCCAGTTCACTGACAAACATGGGGAAGTGTGCCCAGCTGGCTGGAA   600
     B GCTGGTCCAGGCCTTCCAGTACACAGACGAGCATGGGGAAGTTTGTCCCGCTGGCTGGAA   654

A ACCTGGCAGTGATACCATCAAGCCTGATGTCCCAAAGACCAAAGAATATTTCTCCAAGCA   660
     B GCCTGGCAGTGACACGATTAAGCCCAACGTGGATGACAGCAAGGAATATTTCTCCAAACA   714

A GAAGTGAGCGCTGGGCTGTTTTAGTGCCAGGCTGCGGTGGGCAGCCATGAGACCCAAACC   720
     B CAATTAGGCTGGCTAACGGATAGTGAGCTTGTGCCCCTGCCTAGGTGCCTGTGCTGGGTG   774

A TCTTCTGTATTTTTTTTTTCCATTAGTAAAACACAAGACTTCAGATTCAGCCGAATTGTG   780
     B TCCACCTGTGCCCCACCTGGGTGCCCTATGCTGACCCAGGAAAGGGCAGCCCTGCCCCT   834

A GTGTCTTACAAGGCAGGCCTTTCCTACAGGGGGTGGAGAGACCAGCCCG             829
     B CCAAACTCCACAAGTATGGGACCCTGGAGGGGTAGGGCAAGGGCCTTCTCAATGCCTCCA   894

B CCTAGAAGTTGAATTGTGAGGCCTCCCCCAAGCCCAACCCAGGCGGACAAAAGGCCTAGA   954

B GGTAACAATAAAGTATTAGGGAAAGGAAAAAAAAAAAAAAAAAAAAAAAAAAAA        1008
```

*Fig. 1.*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 600 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( v i i i ) POSITION IN GENOME:
( C ) UNITS: bp ( i x ) FEATURE:
( A ) NAME/KEY: CDS
( B ) LOCATION: 1..532

( i x ) FEATURE:
( A ) NAME/KEY: CDS
( B ) LOCATION: 1..600

( x i ) SEQUENCE DESCRIPTION: SEQ ID NO:1:

```
ATG  TCT  TCA  GGA  AAT  GCT  AAA  ATT  GGG  CAC  CCT  GCC  CCC  AAC  TTC  AAA        48
Met  Ser  Ser  Gly  Asn  Ala  Lys  Ile  Gly  His  Pro  Ala  Pro  Asn  Phe  Lys
 1                   5                        10                       15

GCC  ACA  GCT  GTT  ATG  CCA  GAT  GGT  CAG  TTT  AAA  GAT  ATC  AGC  CTG  TCT        96
Ala  Thr  Ala  Val  Met  Pro  Asp  Gly  Gln  Phe  Lys  Asp  Ile  Ser  Leu  Ser
                     20                       25                       30

GAC  TAC  AAA  GGA  AAA  TAT  GTT  GTG  TTC  TTC  TTT  TAC  CCT  CTT  GAC  TTC       144
```

|  |  |  |  |  |  |  |  |  |  |  |  |  |  |  |  |
|---|---|---|---|---|---|---|---|---|---|---|---|---|---|---|---|
| Asp | Tyr | Lys | Gly | Lys | Tyr | Val | Val | Phe | Phe | Phe | Tyr | Pro | Leu | Asp | Phe |
|  |  | 35 |  |  |  | 40 |  |  |  |  |  | 45 |  |  |  |

| ACC | TTT | GTG | TGC | CCC | ACG | GAG | ATC | ATT | GCT | TTC | AGT | GAT | AGG | GCA | GAA | 192 |
|---|---|---|---|---|---|---|---|---|---|---|---|---|---|---|---|---|
| Thr | Phe | Val | Cys | Pro | Thr | Glu | Ile | Ile | Ala | Phe | Ser | Asp | Arg | Ala | Glu |  |
|  | 50 |  |  |  | 55 |  |  |  |  | 60 |  |  |  |  |  |  |

| GAA | TTT | AAG | AAA | CTC | AAC | TGC | CAA | GTG | ATT | GGT | GCT | TCT | GTG | GAT | TCT | 240 |
|---|---|---|---|---|---|---|---|---|---|---|---|---|---|---|---|---|
| Glu | Phe | Lys | Lys | Leu | Asn | Cys | Gln | Val | Ile | Gly | Ala | Ser | Val | Asp | Ser |  |
| 65 |  |  |  | 70 |  |  |  | 75 |  |  |  |  | 80 |  |  |  |

| CAC | TTC | TGT | CAT | CTA | GCA | TGG | GTC | AAT | ACA | CCT | AAG | AAA | CAA | GGA | GGA | 288 |
|---|---|---|---|---|---|---|---|---|---|---|---|---|---|---|---|---|
| His | Phe | Cys | His | Leu | Ala | Trp | Val | Asn | Thr | Pro | Lys | Lys | Gln | Gly | Gly |  |
|  |  |  |  | 85 |  |  |  | 90 |  |  |  |  | 95 |  |  |  |

| CTG | GGA | CCC | ATG | AAC | ATT | CCT | TTG | GTA | TCA | GAC | CCG | AAG | CGC | ACC | ATT | 336 |
|---|---|---|---|---|---|---|---|---|---|---|---|---|---|---|---|---|
| Leu | Gly | Pro | Met | Asn | Ile | Pro | Leu | Val | Ser | Asp | Pro | Lys | Arg | Thr | Ile |  |
|  |  |  | 100 |  |  |  | 105 |  |  |  | 110 |  |  |  |  |  |

| GCT | CAG | GAT | TAT | GGG | GTC | TTA | AAG | GCT | GAT | GAA | GGC | ATC | TCG | TTC | AGG | 384 |
|---|---|---|---|---|---|---|---|---|---|---|---|---|---|---|---|---|
| Ala | Gln | Asp | Tyr | Gly | Val | Leu | Lys | Ala | Asp | Glu | Gly | Ile | Ser | Phe | Arg |  |
|  |  | 115 |  |  |  | 120 |  |  |  | 125 |  |  |  |  |  |  |

| GGC | CTT | TTT | ATC | ATT | GAT | GAT | AAG | GGT | ATT | CTT | CGG | CAG | ATC | ACT | GTA | 432 |
|---|---|---|---|---|---|---|---|---|---|---|---|---|---|---|---|---|
| Gly | Leu | Phe | Ile | Ile | Asp | Asp | Lys | Gly | Ile | Leu | Arg | Gln | Ile | Thr | Val |  |
|  | 130 |  |  |  | 135 |  |  |  | 140 |  |  |  |  |  |  |  |

| AAT | GAC | CCT | CCC | TGT | TGC | CGC | TCT | GTG | GAT | GAG | ACT | TTG | AGA | CTA | GTT | 480 |
|---|---|---|---|---|---|---|---|---|---|---|---|---|---|---|---|---|
| Asn | Asp | Pro | Pro | Cys | Cys | Arg | Ser | Val | Asp | Glu | Thr | Leu | Arg | Leu | Val |  |
| 145 |  |  |  | 150 |  |  |  | 155 |  |  |  |  | 160 |  |  |  |

| CAG | GCC | TTC | CAG | TTC | ACT | GAC | AAA | CAT | GGG | GAA | GTG | TGC | CCA | GCT | GGC | 528 |
|---|---|---|---|---|---|---|---|---|---|---|---|---|---|---|---|---|
| Gln | Ala | Phe | Gln | Phe | Thr | Asp | Lys | His | Gly | Glu | Val | Cys | Pro | Ala | Gly |  |
|  |  |  | 165 |  |  |  | 170 |  |  |  | 175 |  |  |  |  |  |

| TGG | AAA | CCT | GGC | AGT | GAT | ACC | ATC | AAG | CCT | GAT | GTC | CCA | AAG | ACC | AAA | 576 |
|---|---|---|---|---|---|---|---|---|---|---|---|---|---|---|---|---|
| Trp | Lys | Pro | Gly | Ser | Asp | Thr | Ile | Lys | Pro | Asp | Val | Pro | Lys | Thr | Lys |  |
|  |  | 180 |  |  |  | 185 |  |  |  | 190 |  |  |  |  |  |  |

| GAA | TAT | TTC | TCC | AAG | CAG | AAG | TGA |  |  |  |  |  |  |  |  | 600 |
|---|---|---|---|---|---|---|---|---|---|---|---|---|---|---|---|---|
| Glu | Tyr | Phe | Ser | Lys | Gln | Lys |  |  |  |  |  |  |  |  |  |  |
|  |  | 195 |  |  |  |  |  |  |  |  |  |  |  |  |  |  |

( 2 ) INFORMATION FOR SEQ ID NO:2:

( i ) SEQUENCE CHARACTERISTICS:
   ( A ) LENGTH: 199 amino acids
   ( B ) TYPE: amino acid
   ( D ) TOPOLOGY: linear ( i i ) MOLECULE TYPE: protein ( x i ) SEQUENCE DESCRIPTION: SEQ ID NO:2:

|  |  |  |  |  |  |  |  |  |  |  |  |  |  |  |
|---|---|---|---|---|---|---|---|---|---|---|---|---|---|---|
| Met | Ser | Ser | Gly | Asn | Ala | Lys | Ile | Gly | His | Pro | Ala | Pro | Asn | Phe | Lys |
| 1 |  |  |  | 5 |  |  |  |  | 10 |  |  |  |  | 15 |  |

| Ala | Thr | Ala | Val | Met | Pro | Asp | Gly | Gln | Phe | Lys | Asp | Ile | Ser | Leu | Ser |
|---|---|---|---|---|---|---|---|---|---|---|---|---|---|---|---|
|  |  |  | 20 |  |  |  |  | 25 |  |  |  |  | 30 |  |  |

| Asp | Tyr | Lys | Gly | Lys | Tyr | Val | Val | Phe | Phe | Phe | Tyr | Pro | Leu | Asp | Phe |
|---|---|---|---|---|---|---|---|---|---|---|---|---|---|---|---|
|  |  | 35 |  |  |  | 40 |  |  |  |  |  | 45 |  |  |  |

| Thr | Phe | Val | Cys | Pro | Thr | Glu | Ile | Ile | Ala | Phe | Ser | Asp | Arg | Ala | Glu |
|---|---|---|---|---|---|---|---|---|---|---|---|---|---|---|---|
|  | 50 |  |  |  | 55 |  |  |  |  | 60 |  |  |  |  |  |

| Glu | Phe | Lys | Lys | Leu | Asn | Cys | Gln | Val | Ile | Gly | Ala | Ser | Val | Asp | Ser |
|---|---|---|---|---|---|---|---|---|---|---|---|---|---|---|---|
| 65 |  |  |  | 70 |  |  |  | 75 |  |  |  |  | 80 |  |  |

| His | Phe | Cys | His | Leu | Ala | Trp | Val | Asn | Thr | Pro | Lys | Lys | Gln | Gly | Gly |
|---|---|---|---|---|---|---|---|---|---|---|---|---|---|---|---|
|  |  |  |  | 85 |  |  |  | 90 |  |  |  |  | 95 |  |  |

| Leu | Gly | Pro | Met | Asn | Ile | Pro | Leu | Val | Ser | Asp | Pro | Lys | Arg | Thr | Ile |
|---|---|---|---|---|---|---|---|---|---|---|---|---|---|---|---|
|  |  |  | 100 |  |  |  | 105 |  |  |  | 110 |  |  |  |  |

| Ala | Gln | Asp | Tyr | Gly | Val | Leu | Lys | Ala | Asp | Glu | Gly | Ile | Ser | Phe | Arg |
|---|---|---|---|---|---|---|---|---|---|---|---|---|---|---|---|
|  |  | 115 |  |  |  | 120 |  |  |  | 125 |  |  |  |  |  |

| Gly | Leu | Phe | Ile | Ile | Asp | Asp | Lys | Gly | Ile | Leu | Arg | Gln | Ile | Thr | Val |
|---|---|---|---|---|---|---|---|---|---|---|---|---|---|---|---|

|     |     |     | 130 |     |     |     |     | 135 |     |     |     |     | 140 |     |     |
| --- | --- | --- | --- | --- | --- | --- | --- | --- | --- | --- | --- | --- | --- | --- | --- |

Asn Asp Pro Pro Cys Cys Arg Ser Val Asp Glu Thr Leu Arg Leu Val
145                 150                 155                 160

Gln Ala Phe Gln Phe Thr Asp Lys His Gly Glu Val Cys Pro Ala Gly
            165                 170                 175

Trp Lys Pro Gly Ser Asp Thr Ile Lys Pro Asp Val Pro Lys Thr Lys
            180                 185                 190

Glu Tyr Phe Ser Lys Gln Lys
            195

( 2 ) INFORMATION FOR SEQ ID NO:3:

( i ) SEQUENCE CHARACTERISTICS:
                ( A ) LENGTH: 537 base pairs
                ( B ) TYPE: nucleic acid
                ( C ) STRANDEDNESS: double
                ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
                ( A ) ORGANISM: Homo sapiens ( i x ) FEATURE:
                ( A ) NAME/KEY: CDS
                ( B ) LOCATION: 1..536

( x i ) SEQUENCE DESCRIPTION: SEQ ID NO:3:

```
ATG GCC TCC GGT AAC GCG CGC ATC GGA AAG CCA GCC CCT GAC TTC AAG    48
Met Ala Ser Gly Asn Ala Arg Ile Gly Lys Pro Ala Pro Asp Phe Lys
 1               5                  10                  15

GCC ACA GCG GTG GTT GAT GGC GCC TTC AAA GAG GTG AAG CTG TCG GAC    96
Ala Thr Ala Val Val Asp Gly Ala Phe Lys Glu Val Lys Leu Ser Asp
                20                  25                  30

TAC AAA GGG AAG TAC GTG GTC CTC TTT TTC TAC CCT CTG GAC TTC ACT   144
Tyr Lys Gly Lys Tyr Val Val Leu Phe Phe Tyr Pro Leu Asp Phe Thr
         35                  40                  45

TTT GTG TGC CCC ACC GAG ATC ATC GCG TTC AGC AAC CGT GCA GAG GAC   192
Phe Val Cys Pro Thr Glu Ile Ile Ala Phe Ser Asn Arg Ala Glu Asp
 50                  55                  60

TTC CGC AAG CTG GGC TGT GAA GTG CTG GGC GTC TCG GTG CCC CTG AAC   240
Phe Arg Lys Leu Gly Cys Glu Val Leu Gly Val Ser Val Pro Leu Asn
 65                  70                  75                  80

ATC CCC CTG CTT GGT GAC GTG ACC AGA CGC TTG TCT GAG GAT TAC GGC   288
Ile Pro Leu Leu Gly Asp Val Thr Arg Arg Leu Ser Glu Asp Tyr Gly
                 85                  90                  95

GTG CTG AAA ACA GAT GAG GGC ATT GCC TAC AGG GGC CTC TTT ATC ATC   336
Val Leu Lys Thr Asp Glu Gly Ile Ala Tyr Arg Gly Leu Phe Ile Ile
            100                 105                 110

GAT GGC AAG GGT GTC CTT CGC CAG ATC ACT GTT AAT GAT TTG CCT GTG   384
Asp Gly Lys Gly Val Leu Arg Gln Ile Thr Val Asn Asp Leu Pro Val
            115                 120                 125

GGA CGC TCC GTG GAT GAG GCT CTG CGG CTG GTC CAG GCC TTC CAG TAC   432
Gly Arg Ser Val Asp Glu Ala Leu Arg Leu Val Gln Ala Phe Gln Tyr
        130                 135                 140

ACA GAC GAG CAT GGG GAA GTT TGT CCC GCT GGC TGG AAG CCT GGC AGT   480
Thr Asp Glu His Gly Glu Val Cys Pro Ala Gly Trp Lys Pro Gly Ser
145                 150                 155                 160

GAC ACG ATT AAG CCC AAC GTG GAT GAC AGC AAG GAA TAT TTC TCC AAA   528
Asp Thr Ile Lys Pro Asn Val Asp Asp Ser Lys Glu Tyr Phe Ser Lys
```

```
                              165                      170                        175
CAC  AAT  TAG                                                                                    537
His  Asn
```

( 2 ) INFORMATION FOR SEQ ID NO:4:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Ser  Gly  Asn  Ala  Arg  Ile  Gly  Lys  Pro  Ala  Pro  Asp  Phe  Lys
  1                  5                      10                       15
Ala  Thr  Ala  Val  Val  Asp  Gly  Ala  Phe  Lys  Glu  Val  Lys  Leu  Ser  Asp
               20                      25                  30
Tyr  Lys  Gly  Lys  Tyr  Val  Val  Leu  Phe  Phe  Tyr  Pro  Leu  Asp  Phe  Thr
          35                      40                      45
Phe  Val  Cys  Pro  Thr  Glu  Ile  Ile  Ala  Phe  Ser  Asn  Arg  Ala  Glu  Asp
     50                      55                      60
Phe  Arg  Lys  Leu  Gly  Cys  Glu  Val  Leu  Gly  Val  Ser  Val  Pro  Leu  Asn
 65                      70                      75                       80
Ile  Pro  Leu  Leu  Gly  Asp  Val  Thr  Arg  Arg  Leu  Ser  Glu  Asp  Tyr  Gly
                85                      90                      95
Val  Leu  Lys  Thr  Asp  Glu  Gly  Ile  Ala  Tyr  Arg  Gly  Leu  Phe  Ile  Ile
              100                     105                    110
Asp  Gly  Lys  Gly  Val  Leu  Arg  Gln  Ile  Thr  Val  Asn  Asp  Leu  Pro  Val
          115                     120                    125
Gly  Arg  Ser  Val  Asp  Glu  Ala  Leu  Arg  Leu  Val  Gln  Ala  Phe  Gln  Tyr
     130                     135                    140
Thr  Asp  Glu  His  Gly  Glu  Val  Cys  Pro  Ala  Gly  Trp  Lys  Pro  Gly  Ser
145                      150                     155                     160
Asp  Thr  Ile  Lys  Pro  Asn  Val  Asp  Asp  Ser  Lys  Glu  Tyr  Phe  Ser  Lys
              165                     170                    175
His  Asn
```

DNA'S ENCODING NATURAL KILLER CELL ENHANCING FACTOR

This is a continuation-in-part of Ser. No. 08/232,189, filed May 3, 1994, now abandoned, which is a continuation-in-part of Ser. No. 07/787,148, filed Nov. 4, 1991, now U.S. Pat. No. 5,250,295, issued Oct. 5, 1993. This invention was made under Grant Number DK from the National Institute of Health. Accordingly, the U.S. government has certain rights in this invention.

BACKGROUND OF THE INVENTION

1. Field of the Invention

The present invention relates generally to essentially pure natural killer-enhancing factor and to recombinant DNA molecules encoding natural killer-enhancing factor. The present invention also relates generally to methods and compositions which are effective in increasing or enhancing the cytotoxic effectiveness of human natural killer cells. More particularly, the present invention relates to the discovery and molecular cloning of two natural killer-enhancing factors: NKEF A and B.

2. Description of Related Art

The publications and other reference material referred to herein to describe the background and the detailed description of the invention and to provide additional detail regarding its practice are hereby incorporated by reference. For convenience, the referenced materials are numerically referenced and grouped in the appended bibliography.

Natural killer (NK) cells are a subset of lymphocytes found in blood and lymphold tissues and especially the spleen. NK cells are derived from bone marrow and appear as large lymphocytes with prominent cytoplasmic granules. They are sometimes referred to as large granular lymphocytes. NK cells are believed to be responsible for natural surveillance against tumor growth and metastasis and are important regulators for hematopoiesis, including erythropoiesis (1–3).

The activity of NK cells has been shown to increase when several different protein products are present. These protein products include interferons, IL-1, IL-2, IL-6, several types of interferon and tumor necrosis factor-$\alpha$ (4–7). In addition, a B cell product termed NK stimulating factor (NKSF) (12) or cytotoxic lymphocyte maturation factor (13), has been reported as another activator of NK cells. All of these proteins have been purified, identified and cloned.

It has also been demonstrated that NK cells express higher cytotoxic activity against tumor cells in the presence of red blood cells (RBC) (8). Red blood cells are the major cellular component of the peripheral blood and occupy up to one-half of the total blood volume. Therefore, NK cells are usually in constant contact with RBC in the blood and, in fact, have a specific receptor, CD2, that facilitates interactions with RBC (9, 10).

The mechanism by which red blood cells enhance NK cell activity is not entirely known. For example, it has not been established whether the red blood cell itself is responsible for enhancing cytotoxicity or if one or more cellular products are responsible. Accordingly, there is a present need to establish the mechanism by which red blood cells enhance NK cell activity. Further, it would be desirable to isolate and identify any specific cellular components or cellular products which cause the observed NK cell enhancement. Such components or factors could then be used together with or apart from the red blood cell to enhance NK cell activity.

SUMMARY OF THE INVENTION

In accordance with the present invention, a protein which is present in red blood cells and which is capable of enhancing NK cell cytotoxicity has been isolated and identified. The protein or NK-enhancing factor (NKEF) has a molecular mass of between 300 and 400 kilodaltons and an apparent molecular weight of 48,000 daltons as measured by SDS-PAGE. NKEF is located in the cytosol of red blood cells. NKEF is water soluble.

In accordance with the present invention, it was discovered that NKEF enhances the cytotoxic activity of NK cells provided that the NKEF is linked to an anchor moiety or support surface. Further, it was discovered that NKEF is effective in increasing NK cell activity when used alone or when used in combination with other NK cell enhancement proteins, such as Interleukin-2.

NKEF in accordance with the present invention is useful in both in vivo and in vitro applications where it is desirable to stimulate NK cell activity. As a feature of the present invention, the NKEF is linked to surfaces, such as the surface of a plastic test well, when the NKEF is used for in vitro testing. When used in vivo, the NKEF may or may not be linked to an anchor moiety which is adapted for introduction into the blood stream or other in vivo system.

As a feature of the present invention, NKEF has been found to not only be effective in enhancing NK cell activity, but to also be effective with IL-2 to induce lymphocyte activation and proliferation. Accordingly, NKEF may be used for combined immunotherapy with cytokines, such as IL-2, tumor necrosis factor, interferon and the like, to increase the function of B cells, T cells, macrophages, NK cells and other leukocytes.

As another feature of the present invention, it was discovered that NKEF is expressed by cells which are not of erythroid origin. Although isolation of NKEF from red blood cell cytosol is the preferred method of obtaining NKEF, other cell types, such as melanoma cells and B lymphoma cells have also been found to express NKEF.

Yet another feature of the present invention, is the cloning and sequencing of two distinct NKEF cDNAs: NKEF A and B. Provided in accordance with the present invention are essentially pure NKEF A and B and recombinant DNA molecules encoding NKEF A and B.

The above discussed and many other features and attendant advantages of the present invention will become readily apparent as the invention is better understood by a reference to the following detailed description.

BRIEF DESCRIPTION OF THE DRAWINGS

FIG. 1 depicts the nucleic acid sequence of NKEF A and B.

DETAILED DESCRIPTION OF THE INVENTION

Figure 2:
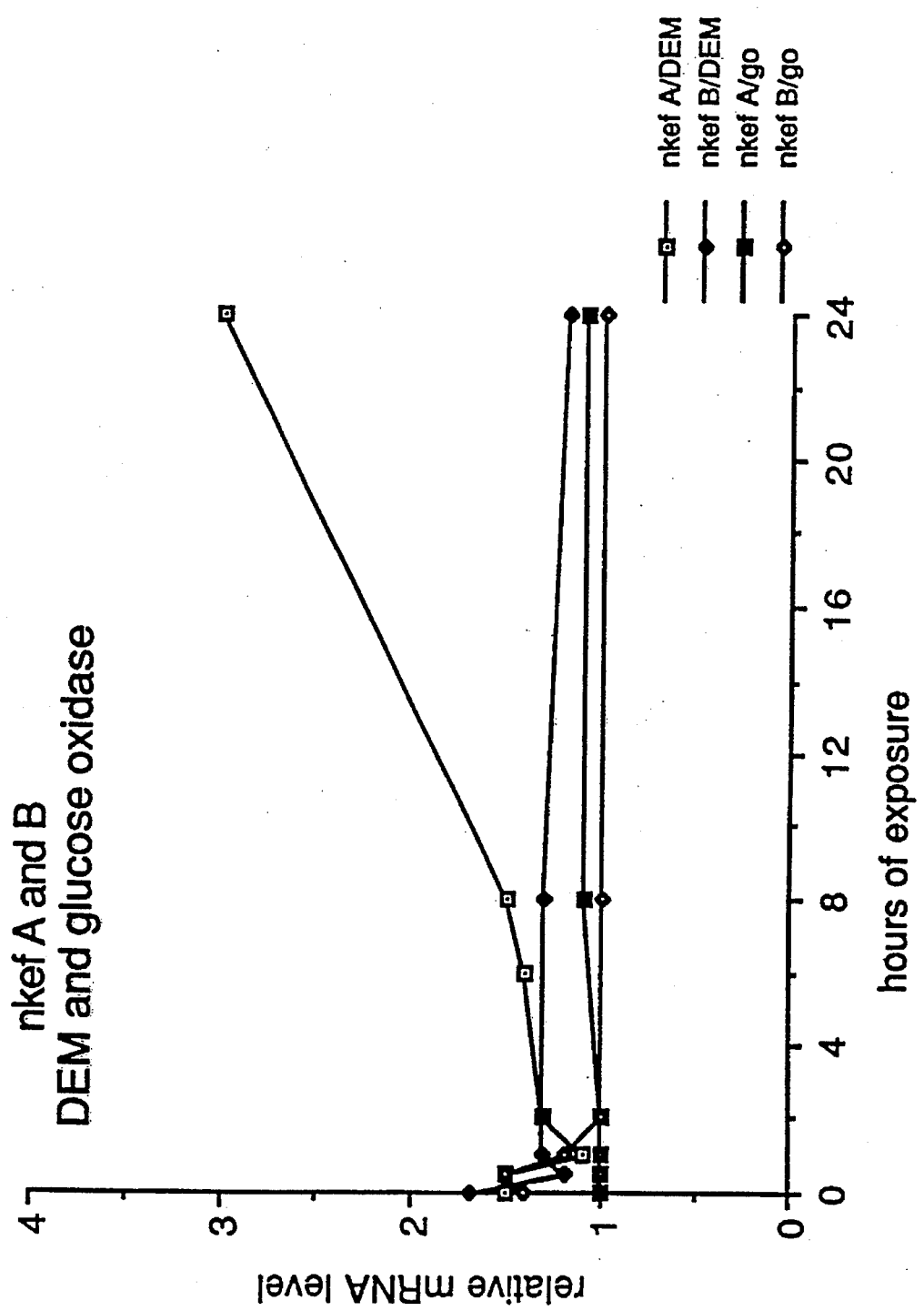
FIG. 2 is a graph depicting the relative levels of NKEF A & B mRNA after exposure of cells to DEM and/or glucose.

The NK-enhancing factor (NKEF) in accordance with the present invention is a water soluble red blood cell protein which is located in the cell cytosol. NKEF has so far only been isolated from human red blood cell cytosol. However, NKEF may also be present in the cytosol of red blood cells present in other mammals. Further, NKEF has been isolated from a melanoma cell line maintained at the University of California at Los Angeles (UCLA) and identified as UCLA-SO-M14. NKEF has also been isolated from a B lymphoma cell line which is also maintained at UCLA and identified as the Raji cell line.

NKEF has a molecular mass of between 300 and 400 kilodaltons as determined by gel filtration chromatography. The apparent molecular weight of NKEF, as determined by sodium dodecyl sulfate polyacrylamide gel electrophoresis (SDS-PAGE) under non-reducing conditions, is about 48 kilodaltons. Under reducing conditions, the apparent molecular weight by SDS-PAGE is about 24 kilodaltons. In regular aqueous solution, NKEF is believed to be a polymer. In the presence of SDS, NKEF appears as a dimer of subunits of the same molecular weights associated by disulfide bonds.

NKEF can be isolated from human red blood cell cytosol and purified using any of the well-known protein separation and purification processes. The initial preparation of the RBC's is preferably accomplished by known centrifugation techniques utilizing density gradients (8). Initial separation of the cytosol from the RBC can also be accomplished according to well known separation techniques. Preferably, the red blood cells are lysed by hypotonic shock with distilled and deionized water (ddH$_2$O). The resulting RBC cytosol and membrane fractions are then preferably separated by centrifugation. The resulting cytosol fraction is preferably suspended in ddH$_2$O prior to further treatment.

A preferred procedure for separating NKEF from the suspended cytosol fraction involves initial precipitation of the protein using ammonium sulfate. Ammonium sulfate is slowly added to the cytosol until the cytosol is 50% saturated with ammonium sulfate. NKEF begins to precipitate from the cytosol at 20% ammonium sulfate saturation. However, 50% saturation is preferred since it provides optimum NKEF recovery without precipitating hemoglobin. Hemoglobin begins to precipitate at ammonium sulfate saturation levels on the order of 60% and higher.

The relatively impure NKEF which is precipitated from the cytosol is preferably further purified using a combination of ion exchange chromatography, dialysis and high pressure liquid chromatography (HPLC). NKEF is easily identified by its molecular mass of 300 to 400 kilodaltons and its apparent molecular weights as determined by SDS-PAGE under non-reducing and reducing conditions.

Once the NKEF has been isolated based on molecular mass and apparent molecular weights, its identity can be further confirmed by comparing the amino acid sequences of tryptic peptides obtained from the NKEF to the amino acid sequences set forth above. Further, the ability of the isolated protein to enhance NK cell activity provides additional confirmation that the appropriate protein has been isolated.

NKEF is useful as a factor to enhance the activity (i.e. cytotoxicity) of NK cells both in vivo and in vitro. For in vitro applications, the NKEF is applied directly to the test well of the microliter tray or other test tray. The effectiveness of NKEF in enhancing NK cell activity is increased substantially when the NKEF is linked or otherwise attached to the surface of the test well. Accordingly, it is preferred that the NKEF be added as an aqueous solution to the test well and allowed to bind to the test well surface for approximately one hour. The excess NKEF is then removed from the well prior to addition of the NK cells, target cells and other test ingredients. The preferred test well material is the plastic commonly used for test trays. Glass and other materials may also be used provided that they do not denature the NKEF. The in vitro uses for NKEF include cytotoxicity assays and other related tests directed to measuring and evaluating NK cell activity.

With respect to in vivo applications, it is believed that NKEF is an effective factor which will enhance the cytotoxic activity of the NK cells provided that the NKEF is linked to an appropriate anchor or carrier moiety before or after it is administered. Anchor moieties which may be linked to NKEF prior to administration include any of the common carrier molecules which are in use including both natural and synthetic polymers.

Exemplary anchor moieties include inert microparticulates, such as ceramics, plastic and glass. Organic anchor moieties include any of the proteins which can link with NKEF without denaturing it and which are capable of being transported with the NKEF through the blood stream or other fluid system in the body. Preferred protein anchor moieties are those which are related to or derived from the red blood cell membrane. Exemplary anchor moieties include polyethylene glycol and liposomes.

The NKEF may also be administered directly to the patient with linkage to a suitable anchor moiety taking place in vivo. When introducing non-anchored NKEF in vivo, it is preferred that the NKEF be protected from undesirable competitive protein binding. Such protection can be provided by encapsulating the NKEF in liposomes or other similar protective barrier.

The dosage ranges for the administration of NKEF are those large enough to produce the desired effect in which the cytotoxic activity of the NK cells show some degree of enhancement or increase. The dosage should not be so large as to cause adverse side effects. Generally, the dosage will vary with the age, condition, sex and extent of the disease in the animal and can be determined by one of skill in the art. The dosage can be adjusted by the individual physician in the event of any counterindications. Dosage can vary from less than 1 mg/kg/dose to about 100 mg/kg/dose, preferably about 5 mg/kg/dose to 10 mg/kg/dose, in one or more dose administrations daily.

NKEF in accordance with the present invention can be administered parenterally by single injections or by gradual infusion over time. NKEF can be administered intravenously, intraperitoneally, intramuscularly, subcutaneously, intracavitarily, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such a ethyl oleate. Aqueous carriers include water, alcoholic/aqueous solutions, emulsions or suspensions, including saline and buffered media. Parenteral vehicles include sodium chloride solution, Ringer's extrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The amino acid sequence of NKEF has been determined by the cloning of cDNAs corresponding to NKEF. cDNAs corresponding to NKEF fell into one of two categories of closely related but non-identical genes, referred to as NKEF A and B. They are 88% identical in amino acid sequence and 71% identical in nucleotide sequences. The nucleotide sequences of NKEF A (Seq. ID NO.1) and B (Seq. ID NO.3) are shown in FIG. 1.

Southern blot analysis suggests that there are 2–3 NKEF family members in the genome (FIG. 2). Analysis of predicted amino acid sequences indicates that both NKEF A and B are cytosol proteins with several phosphorylation sites each, but that they have no glycosylation sites. They are significantly homologous to several other proteins from a wide variety of organisms ranging from prokaryotes to mammals, especially with regard to several well conserved motifs within the amino acid sequences. The biological functions of these proteins in other species are mostly unknown, but some of them were reported to be induced by oxidative stress. Therefore, besides immunoregulation of NK activity, NKEF may be important for cells in coping with oxidative insults.

The present invention also relates to recombinant DNA molecules which encode natural killer enhancing factors ("NKEF"). The synthesis of these DNA molecules may be achieved by methods well known in the art. For example, the recombinant DNA molecules may be obtained from a cDNA library from K562 cells. The synthesis of cDNA libraries and the choice of vectors into which the cDNAs may be inserted are conventional techniques (14).

A wide variety of techniques are available to those of ordinary skill in the art for the localization and identification of cDNAs corresponding to natural killer enhancing factors according to the present invention. The most preferred methods are (1) using an oligonucleotide probe corresponding to the coding sequence of a natural killer enhancing factor to detect cDNA clones expressing the corresponding natural killer enhancing factor and (2) using antibody against a natural killer cell enhancing factor to detect DNA clones expressing the corresponding factor. Employment of the latter technique requires that the cDNA be inserted in a vector capable of expressing it. These vectors include for example λ gt11 and other expression vectors known in the art.

The antibodies used to screen for a natural killer enhancing factor may be raised against native natural killer enhancing factor, against denatured natural killer enhancing factor or against peptide fragments of a natural killer enhancing factor. After a eDNA corresponding to a natural killer enhancing factor has been identified, it may be analyzed by techniques known to those of skill in the art such as sequencing or restriction analysis to determine if it encodes a full length cDNA. Partial cDNA clones may be used to screen for full length cDNA clones.

Sources of cDNA encoding a natural killer enhancing factor include human red blood cells, other mammalian red blood cells, the erythroleukemic cell line K562, and other cell lines of erythroid lineage. Natural killer enhancing factor derived from other than human sources would be expected to have the ability to enhance the activity of natural killer cells from the particular organism from which the factor is derived and in addition would be expected to have substantial similarity to the amino acid sequence of natural killer enhancing factors A or B as set forth in Seq. ID NOS.2 and 4, respectively.

The term "substantial similarity" as used herein in accordance with the present invention denotes a characteristic of a polypeptide sequence or nucleic acid sequence, wherein the polypeptide sequence has at least 70 percent sequence identity compared to a reference sequence, and the nucleic acid sequence has at least 80 percent sequence identity compared to a reference sequence. The percentage of sequence identity is calculated excluding small deletions or additions which total less than 35 percent of the reference sequence. The reference sequence may be a subset of a larger sequence, such as those in Seq. ID NOS. 1 and 3; however, the reference sequence is at least 18 nucleotides long in the case of polynucleotides and at least 6 amino acid residues long in the case of a polypeptide.

It will be appreciated by those of ordinary skill that, due to the degeracy of the genetic code, many different synthetic or recombinant DNAs will be capable of encoding any particular natural killer enhancing factor as set forth in the present invention. Further, a person of ordinary skill will also appreciate that many of these DNAs will be expressed in hosts transformed with them. Therefore, the present invention relates to all recombinant DNA molecules which encode a desired natural killer enhancing factor and which can be expressed with a host transformed therewith.

It is apparent to one of skill in the art that nucleotide substitutions, deletions and additions may be incorporated into the recombinant DNA molecules of the present invention. However, such nucleotide substitutions, deletions and additions should not substantially disrupt the ability of the recombinant DNA molecules to hybridize to the sequences set forth in Seq. ID NOS. 1 and 3 under hybridization conditions that are sufficiently stringent to result in specific hybridization.

The recombinant DNA molecules of the present invention may be inserted into and expressed using a wide variety of vectors. Useful vectors include, for example, known derivatives of SV40, known bacterial plasmids such as *E. coli* plasmids colE1, pCRI and pBR322, phage based vectors such as, for example, derivatives of λ phage, filamentous single-stranded DNA phage based vectors such as M13, yeast vectors such as the 2 micron plasmid, vectors useful in animal cells such as those with animal viral sequences, and vectors derived from combination of phage and plasmid DNA.

The expression vectors used to express a natural killer enhancing activity will generally contain an expression control or promoter sequence operably linked to the natural killer enhancing factor. The promoter or control sequences are chosen such that they are compatible with the host cell in that they control or regulate the expression of a particular DNA sequence.

Exemplary promoter or expression control sequences suitable for use with prokaryotic hosts include the β-lactamase and lactose promoter systems (16, 17) alkaline phosphatase, the tryptophan (trp) promoter system (18) and hybrid promoters such as the tac promoter (19). However, other functional bacterial promoters are suitable. Their nucleotide sequences are generally known, thereby enabling a skilled worker operably to ligate them to DNA encoding an NKEF (20) using linkers or adapters to supply any required restriction sites. Promoters for use in bacterial systems also will contain a Shine-Dalgarno (S.D.) sequence operably linked to the DNA encoding sialyltransferase.

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in Saccharomyces, the plasmid YRp7, for example (21, 22, 23) is commonly used. This plasmid already contains the trp1 gene which provides a selection marker for a mutant strain of yeast lacking the ability to grow in tryptophan, for example ATCC no. 44076 or PEP4-1 (24). The presence of the trp1 lesion as a characteristic of the yeast host cell genome then provides an effective environment for detecting transformation by growth in the absence of tryptophan.

Preferred promoters controlling transcription from vectors in mammalian host cells may be obtained from various sources, for example, the genomes of viruses such as: polyoma, Simian Virus 40 (SV40), adenovirus, retroviruses, hepatitis-β virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (25). The immediate early promoter of the human cytomegalovirus is conveniently obtained as a HindIII E restriction fragment (26). Of course, promoters from the host cell or related species also are useful herein.

The DNA sequences according to the present invention may be introduced into an expression vector via restriction sites present in the vector. The restriction sites are generally designated by virtue of the restriction enzyme which cuts them. Joinder of a DNA sequence to an expression vector such that the sequence is expressed or not is well known to those of skill in the art.

Persons of skill in the art will recognize that not all expression vector/host combinations will work equally in expressing the DNA sequences according to the present invention or in producing a natural killer enhancing factor. However, a person of ordinary skill may make an appropriate selection of an expression vector/host combination in light of the principals set forth herein. Particular considerations for those of ordinary skill include compatibility of the host and vector, toxicity of the produced protein to the host, ease of recovery of the produced protein, etc.

Amino acid sequence variants of a natural killer enhancing factor fall into one or more of three classes: substitutional, insertional or deletional variants. These variants ordinarily are prepared by site specific mutagenesis of nucleotides in the DNA encoding the NKEF, thereby producing DNA encoding the variant, and thereafter expressing the DNA in recombinant cell culture. However, variant NKEF fragments having up to about 100–150 residues may be conveniently prepared using in vitro synthesis. Amino acid sequence variants are characterized by the predetermined nature of the variation, a feature that sets them apart from naturally occurring allelic or interspecies variation of the NKEF amino acid sequence. Amino acid sequence variants will, however, exhibit the biological activity of NKEF, i.e. enhancing the activity of natural killer cells.

While the site for introducing an amino acid sequence variation is predetermined, the mutation per se need not be predetermined. For example, in order to optimize the performance of a mutation at a given site, random mutagenesis may be conducted at the target codon or region and the expressed NKEF variants screened for the optimal combination of desired activity. Techniques for making substitution mutations at predetermined sites in DNA having a known sequence are well known, for example M13 primer mutagenesis or PCR based mutagenesis.

Amino acid substitutions are typically of single residues; insertions usually will be on the order of about from 1 to 10 amino acid residues; and deletions will range from about 1 to 30 residues. Deletions er insertions preferably are made in adjacent pairs, i.e. a deletion of 2 residues or insertion of 2 residues. Substitutions, deletions, insertions or any combination thereof may be combined to arrive at a final construct. Obviously, the mutations that will be made in the DNA encoding the variant NKEF must not place the sequence out of reading frame and preferably will not create complementary regions that could produce secondary mRNA structure.

The above disclosure generally describes the present invention. A further understanding can be obtained by reference to the following specific examples which are provided for purposes of illustration and are not intended to be limiting.

ISOLATION AND PURIFICATION OF NKEF

Peripheral blood lymphocytes (PBL) and RBC from healthy donors were prepared by centrifugation over density gradients as previously described (6). PBL were resuspended in culture medium (CM) which was RPMI1640 supplemented with 10% heat-inactivated human AB serum, and were used as effector cells for NK cytotoxicity assay. To obtain subcellular components of RBC, RBC were lysed by hypotonic shock with 10 volumes of distilled deionized water (ddH$_2$O).

RBC cytosol and membrane fractions were then separated by centrifugation at 20,000×g for 15 minutes. The RBC membrane fraction was washed 3 times with ddH$_2$O, centrifuged and resuspended in one third of the volume of ddH$_2$O that was used to suspend the cytosol.

The NKEF was initially separated from the cytosol by slowly adding ammonium sulfate to RBC cytosol. The precipitated molecules were dissolved with the original volume of phosphate buffered saline (PBS) and twice reprecipitated with same concentration of ammonium sulfate. The precipitated fractions and the soluble fractions were extensively dialyzed against buffer before testing NKEF activity. The NKEF was precipitated by as little as 20% saturated ammonium sulfate. In contrast, hemoglobin precipitated at above 60% saturated ammonium sulfate. Therefore, for optimal recovery of NKEF with minimal hemoglobin contamination, 50% saturated ammonium sulfate was chosen as the concentration for purification of NKEF.

The ammonium sulfate precipitated NKEF was further purified by ion exchange chromatography and tested for NKEF activity. The partially purified NKEF was dialyzed against 20 μM of tris-HCl buffer (pH 8.0) and applied to a Q-Sepharose column (LKB-Pharmacia) (2×30 cm) pre-equilibrated with the same buffer. The column was eluted with 400 ml of a 0 to 2M NaCl gradient at 4 ml/2 min/fraction. The NaCl in eluted fractions was dialyzed out against tris-HCl buffer before testing for NKEF activity. The NaCl in the eluted fractions may be left in since it does not change NKEF activity in the Q-Sepharose separated fractions.

After Q-Sepharose separation, NKEF was further purified by HPLC with a TSK 250 gel filtration column. Ammonium sulfate and Q-Sepharose separated NKEF was applied to an Bio-Sil TSK-250 gel filtration column (300×7.5 mm) (Bio-Rad, Richmond, Calif.) and eluted with 20 mM tris-HCl (pH 8.0) buffer at the rate of 1 ml/min/fraction. The major protein peak was detected between 7 and 8 minutes after sample injection. Both the protein peak and the NKEF activity peak were detected in fraction 8. The molecular mass of NKEF was estimated to be between 300 and 400 kilodaltons by comparing elution volumes with known molecular weight markers. The overall results of NKEF purification achieved by these purification steps are summarized in Table 1.

TABLE 1

Purification of NKEF

| Purification Steps | Total Protein (mg) | Total Activity (u)[a] | Specific Activity (u/mg) | Purification (fold) | Yield (%) |
|---|---|---|---|---|---|
| Cytosol | 4080 | 17136 | 4.2 | 1 | 100 |
| $(NH_4)_2SO_4$ | 81 | 6002 | 74.1 | 17.6 | 35 |
| Q-Sepharose | 5.52 | 690 | 125 | 29.8 | 4 |
| TSK-250 | 0.06 | 100 | 1667 | 396.9 | 0.6 |

[a]One unit of activity is defined as the minimum amount of protein needed to significantly increase NK activity as indicated by a p<0.05 by Student's t test.

CHARACTERIZATION OF NKEF

To characterize NKEF and determine whether it is a protein, partially purified NKEF was incubated and treated with 12.5 mg/ml of porcine pancreas trypsin for 18 hr. at 37° C. and then tested for NKEF activity. Trypsin treated NKEF was then used to coat microwells to determine the effect on NK cytotoxicity. As controls, NKEF and trypsin were separately treated in similar conditions. Both RBC cytosol and NKEF partially purified by 50% saturated ammonium sulfate have been tested with similar results.

The treatment of NKEF with trypsin totally abolishes its activity demonstrating that a protein component is responsible for NKEF activity. Trypsin alone, after overnight incubation and dilution to the level in the assay medium, had no direct effect on NK activity.

NKEF purity and molecular weight estimates were measured by SDS-PAGE (11) with 12% slab gels. For reducing conditions, the samples were treated with 2.5 % of 2-mercaptoethanol. For non-reducing conditions, the samples were treated with 300 mM of N-ethlymalimide. The molecular weight of NKEF was estimated from prestained standards in parallel lanes (Bio-Rad, Richmond, Calif.). Under non-reducing conditions, NKEF appeared as a single band at 48,000 daltons position of the gels. In reducing gels, NKEF appeared as a 24,000 dalton band. SDS-PAGE of a reduced sarapie of NKEF exhibits a very faint band at 48,000 daltons as well, which is believed to be residual unreduced NKEF. The SDS-PAGE results show that NKEF is a dimer of subunits of same molecular weights associated by disulfide bonds. The HPLC results show that these dimers aggregate non-covalently to form polymers of between 300 kilodaltons and 400 kilodaltons mass in aqueous solution.

A specific serum against human NKEF was also generated. The 24,000 dalton band of SDS-PAGE purified NKEF was cut from the reduced gels, squeezed through a 18 gauge syringe needle, mixed with equal volumes of Freund's complete adjuvant and injected into rabbits. After several injections the rabbits were bled and the immune sera were tested for antibody against NKEF by Western blot analysis and ELISA. Results from ELISA show that immune but not pre-immune rabbit serum reacts strongly with RBC cytosol. Western blot analysis of the reduced gel indicates that the immune serum reacts with a 24,000 dalton component in human RBC cytosol. A faint band is sometimes detected at the 48,000 dalton position by Western Blot. The reactivity of the polyclonal antibody to the band at 48,000 daltons indicates that not all of the NKEF in the sample was reduced to its monomer.

IDENTIFICATION OF NKEF FROM K562 CELLS

Since NK sensitive K562 tumor cells are of erythroid linkage, the existence of NKEF in K562 cytosol was verified. To prepare K562 cytosol, the K562 cells were washed three times with Dulbecco's phosphate buffered saline (PBS). The cells were then resuspended in PBS at $2 \times 10^7$ cells/ml. After 3 cycles of freezing and thawing, the cell lysate was microfuged at 10,000 rpm for 2 minutes and the cytosol was harvested for testing. RBC cytosol and K562 cytosol (10 µl/well) at a number of different protein concentrations were added into ELISA plates, incubated for 1 hr. at 37° C., and washed with phosphate buffered saline (pH 7.2). The plates were coated with 100 µl of 2% fetal bovine serum in PBS for another 1 hr. and washed. Rabbit sera (1/100 dilution, 100 µl/well) were added and incubated for 1 hr. After washing, goat anti-rabbit Ig-conjugated with alkaline phosphatase (Sigma, St. Louis, Mo.) (1/1000 dilution, 100 µl/well) was added. Color was developed by adding ponitrophenyl phosphate 2 mg/ml in diethanolamine buffer, pH 9.8, 200 µl/well) after washing with PBS and 0,2% Triton X-100. Optical density was measured at 405 nm.

The ELISA tests show that rabbit anti-NKEF antibody also reacts with K562 cytosol.

Samples containing NKEF from both RBC and K562 cytosol were treated with 2.5% 2-mercaptoethanol and separated by SDS-PAGE (11) with a 12% slab gel. Immediately following separation by SDS-PAGE the gel was treated with transfer buffer and blotted onto a nitrocellulose paper (11). After blocking with 5% human serum albumin in blocking buffer, the nitrocellulose paper was incubated with 1/1000 dilution of rabbit anti-human NKEF serum for 16 hr. at room temperature. The nitrocellulose paper was washed, and treated with 1/500 dilution of goat anti-rabbit Ig conjugated with alkaline phosphatase for 2 hr. at room temperature. After washing the color was developed by adding BCIP/NBT substrate (Bethesda Research Laboratories, Gaithersburg, Md.). The molecular masses of the bands were determined from the prestained standards (Bio-Rad, Richmond, Calif.) in parallel lanes. Western blot analysis confirmed that the KNEF from K562 cytosol has the same 24,000 daltons molecular weight as that from RBC. A faint band was also sometimes detected at 48,000 daltons by Western blot analysis in the K562 cytosol and RBC cytosol.

In addition, cytospin slides of K562 were fixed with acetone for 1 hr., then treated with 2% NP-40 for 30 min. The slides were sequentially washed and treated with rabbit anti-NKEF serum and alkaline phosphatase conjugated goat anti-rabbit Ig. The color was developed by adding BCIP/NBT substrate. Immunohistological staining of K562 with anti-NKEF serum shows that this factor is present in K562 cytosol.

The test used to measure NK activity was the standard 4 hour chromium release using K562 erythroleukemic cells as target cells (8). The K562 erythroleukemic cell line was maintained in 10% fetal bovine serum and RPMI1640 medium supplemented with antibiotics. 5000 [$^{51}$Cr] labeled K562 cells were added with peripheral blood lymphocytes (PBL) in round bottom microwells and centrifuged for 4 minutes at 50×g to initiate cytotoxicity. Total volume of culture medium in each well was 200 µl. After a 4 hour incubation at 37° C., 100 µl of supernate was collected from each well for measuring radioactivity released from killed K562 cells. The effector cell:target ratio used was 40:1 unless indicated otherwise below. Percent cytolysis was calculated as [(Observed cpm−spontaneous cpm)/(Maximal cpm−spontaneous cpm)]×100%. Each assay was done in triplicate and the results are presented as % cytotoxicity±S.E.M.

To test for NKEF activity, different samples were added into microwells (100 µl/well) before the NK assay and incubated at 37° C. for 1 hour. The microwells were washed 3 times with PBS and then incubated for another 1 hr. at 37° C. with 100 μl of culture medium. After removal of the culture media, PBL and K562 were added to the microwells to initiate the NK assay. NKEF activity was indicated by an increase of NK cytolysis over control that is significant at the 0.05 level.

RBC cell lysates containing NKEF, when coated on the plastic surface of microliter wells, enhance NK cytotoxicity. To verify that NKEF enhances NK activity, the RBC cytosol and membrane were separately coated on the surface of microliter wells and tested for effects on cytotoxicity. It was found that NK activity is significantly increased in the microwells pre-coated with RBC cytosol. The increase was observed in all three effector cell:target cell ratios tested as compared with control wells. In contrast, NK activity in wells coated with RBC membrane showed no increase over controls. No difference in NK activity was observed between untreated wells, wells coated with PBS, and wells coated with 10% human AB serum (data not shown).

While RBC cytosol-coated wells enhance NK activity, addition of RBC cellular components directly into chromium release assays had no effect on NK cytotoxicity. Neither RBC cytosol or membrane, nor the combination of these two components, significantly influenced NK activity when added into the assay. Where RBC membrane and cytosol were compared, the microwells were pretreated with 0.5% glutaldehyde for 30 min. at 37° C. before coating with the membrane preparations in order to anchor RBC membrane on the plastic. The glutaldehyde treatment had neither a direct effect on NK activity nor did it influence regulation of NK by RBC cytosol or membrane. These results show that NKEF is a water soluble protein located in the RBC cytosol, but not the RBC membrane. These results also demonstrate that NK cell activity is enhanced when NKEF is linked to an anchor molecule.

ENHANCEMENT OF IL-2 INDUCTION OF LAK CELLS

NKEF also enhances interleukin-2 (IL-2) induction of lymphokine activated killer (LAK) cell function and proliferation. NKEF partially purified from RBC cytosol by 50% saturated ammonium sulfate and Q-Sepharose ion exchange chromatography was coated on the surface of tissue culture wells and washed as described above. PBL ($10^6$ cell/ml) were cultured at 37° C. in the tissue culture wells in the presence of recombinant human IL-2 analog (ser 125) (Amgen, Inc., Thousand Oaks, Calif.) for 4 days. The lymphocytes were then collected and tested for cytotoxicity in a 4 hr. chromium release assay using the melanoma UCLA-SO-M14 (M14) cell line as target cells with 4 different effector cell:target cell ratios ranging from 20:1 to 2.5:1. Results in Table 2 show that NKEF pre-coated on the plastic greatly enhances IL-2 induction of LAK cytotoxicity both at high (100 u/ml) and low (10 (u/ml) concentrations of IL-2.

NKEF added in solution also significantly enhances LAK induction. Without IL-2, no LAK activity is induced even in the presence of NKEF. The results are expressed as lytic unit (LU)±SD per $10^6$ effector cells. Each LU is defined as the number of effector cells required to lyse 30% of the target cells (13).

TABLE 2

| NKEF Enhances LAK Induction | |
|---|---|
| Treatment of PBL | Lytic unit ± SD |
| IL-2 (100 u/ml) | 27.7 ± 3.1 |
| IL-2 + NKEF on plastic | 44.3 ± 7.3 |
| IL-2 + NKEF in solution | 44.1 ± 5.6 |
| IL-2 (10 u/ml) | 4.9 ± 0.8 |
| IL-2 + NKEF on plastic | 13.9 ± 1.9 |
| IL-2 + NKEF in solution | 8.7 ± 0.7 |

The proliferative response of lymphocytes was measured by incorporation of tritiated thymidine. Lymphocytes collected from 4 day IL-2 cultures were seeded in triplicate in microwells ($10^5$ cells/200 μul/well) and pulsed with 0.5 μCi/well of $^3$H-thymidine (6.7 Ci/mmole) for 4 hr. at 37° C. in a humidified incubator with 5% $CO_2$. The cells were harvested by a PhD harvester (Cambridge Technology, Cambridge, Mass.) and the thymidine incorporated was measured by a scintillation counter.

Similar to LAK induction, IL-2 induced PBL proliferation is also greatly augmented by plastic-anchored NKEF as set forth in Table 3. This enhancement was observed both at high (100 u/ml) and low (10 u/ml) concentrations of IL-2. NKEF in the solution also enhances IL-2 induced PBL proliferation. Without IL-2, NKEF alone does not induce lymphocyte proliferation.

In view of these results, it is believed that NKEF will be effective when combined with IL-2 or other cytokines to induce lymphocyte activation and proliferation. NKEF will be useful for combined immunotherapy with cytokines, such as IL-2, tumor necrosis factor, interferon and the like, to increase the function of B cells, T cells, macrophages, NK cells and other leukocytes.

TABLE 3

| NKEF Enhances IL-2 Induced PBL Proliferation | |
|---|---|
| Treatment | cpm ± SD |
| IL-2 (100 u/ml) | 8728 ± 563 |
| IL-2 + NKEF on plastic | 16446 ± 211 |
| IL-2 + NKEF in solution | 12036 ± 1340 |
| IL-2 (10 u/ml) | 1683 ± 105 |
| IL-2 + NKEF on plastic | 4362 ± 473 |
| IL-2 + NKEF in solution | 6120 ± 2735 |

CLONING AND CHARACTERIZATION OF NKEF A & B

MATERIALS AND METHODS
Cells

K562 cells were originally obtained from a patient diagnosed with myeloleukemia, but was later found to express characteristics of erythroid lineage (27). The cells are grown in RPMI1640 medium (BioWhittaker, Walkersville, Md.) supplemented with 10% fetal bovine serum (Gemini Bioproducts, Calabassis, Calif.), HEPES buffer (CalBiochem, San Diego, Calif.) and antibiotics (PSF, BioWhittaker, 100 u/ml Penicillin. 100 μg/ml Streptomycin, 0.25 μg/ml Fungizone). For mRNA purification (for subsequent primer extension and sequencing), 1–3×$10^8$ K562 cells were harvested using the Fast Track mRNA purification kit (Invitrogen, San Diego, Calif.). Resultant mRNA was quantified spectrophotometrically.

13

Immunoblot screening

Specific antibody against human NKEF proteins was raised in a rabbit as described (28). This antibody recognizes a protein in RBC and K562 with the same Mr as NKEF and blocks NKEF activity. The anti-NKEF antibody was used as a probe to screen a λgt11 cDNA expression library of K562 (Clontech Laboratories, Palo Alto, Calif.) with protocols as described in (14;15). Mouse monoclonal anti-rabbit Ig conjugated with alkaline phosphatase (Sigma Chemicals, St. Louis, Mo.) was used as a secondary antibody in the immunoblot screening. The BCIP/NBT substrate system (Bethesda Research Laboratories, Gaithersburg, Md.) was used for color development. Positive plaques were picked and rescreened several times to homogeneity.

To obtain additional NKEF clones, the cDNA library was probed by standard plaque hybridization utilizing cDNA probes that were obtained by the initial immunological screening. Positive plaques were detected using the non-isotopic Genius system detection kit (Boehringer Mannheim, Indianapolis, Ind.) according to the manufacturer's instructions.

Sequencing of NKEF cDNAs cDNA inserts of the clones were isolated from the EcoRI site of the λgt11 vector, and cloned into the EcoRI site of pUC18 plasmid vectors as described in (14). pUC18 DNAs carrying NKEF inserts were manually sequenced according to the Sanger method on denatured duplex templates. Specific oligonucleotide primers based on newly acquired end sequences were synthesized (Bio-Synthesis, Lewisville, Tex.; UCLA Fermenter/Preparation Core Facility) and used for further sequencing on both strands. The automated sequencing was performed by the UCLA Sequencing Core Facility on an ABI 373A DNA Sequencer to complete the cDNA sequencing.

Primer Extension and mRNA Sequencing

Primer extension was performed by utilizing Promega's (Madison, Wis.) Primer Extension kit with K562 mRNA and an NKEF-specificoligonucleotide according to the manufacturer's instructions. The 30 nucleotide NKEF A specific oligonucleotide was designed using previously identified 5' cDNA sequence and stacking energies from the GCG "Fold" program. Direct sequencing of the NKEF A mRNA was performed using the Promega primer extension kit (Madison, Wis.), an mRNA sequencing protocol (29) and the following modifications: 12 μg mRNA+5 ng $^{32}$P-end labelled 30 nucleotide oligo primer were annealed in 1× AMV RT (Avian Myeloblastsis Virus Reverse Transcriptase) buffer at 80° C. for 3 minutes, 65° C. for 45 minutes and room temperature for 20 minutes. The annealed mixture was then divided into four tubes for the four dideoxy termination reactions. To each tube was added an equal volume of a 2× sequencing mixture containing 2× AMV RT buffer/5 mM sodium pyrophosphate/0.1 mg/ml actinomycin D/2 mM dNTP mix/and 0.75 u/μl AMV RT enzyme. Lastly, one ddNTP was added per tube (such that the final ddNTP concentration was 0.76 mM ddA and ddC, 0.38 mM ddG and 1.5 mM ddT). The reactions were incubated at 50° C. for 30 minutes, then denatured and run on an 8% Long Ranger/Tris-Taurine-EDTA (United States Biochemicals) sequencing gel. The dried gel was autoradiographed.

Sequence Analysis

All of the resultant sequence information was compiled and analyzed using the University of Wisconsin'c Genetics Computer Group (GCG) software package. DNA and protein databases were searched primarily at the NCBI using the Blast network service. The two NKEF sequences, A and B, have been assigned the Genbank accession numbers L19184 and L19185, respectively.

14

Genomic Southern Blot

To prepare the genomic Southern blot, genomic DNA was purified from K562 cells by taking $5\times10^7$ cells washed twice in PBS, resuspending them in 5 ml 10 mM Tris HCl pH 8.0/100 mM NaCl/10 mM EDTA and lysing them in the same buffer plus 2% Sarkosyl and 500 /μg/ml proteinase K at 50° C. over night. The lysate was extracted with phenol/chloroform three times and precipitated in 0.1 vol. 3M Na OAc/1.5 vol. isopropanol. The DNA was removed on a pipette tip, and resuspended in TE. Thirty micrograms of the genomic DNA (per lane) was digested with either BamHI or EcoRI and loaded onto an agarose gel. DNA was transferred to a Magnacharge (Micron Seperations, Inc., Westboro, Mass.) nylon membrane by vacuum blotting and probed with NKEF A or B cDNA probes utilizing the Genius System non-isotopic detection kit(according to the manufacturers instructions). Blots were washed at both high stringency (65° C.) and lower stringency (55° C.) temperatures. Resultant bands were visualized by chemiluminescence.

RESULTS

The specific anti-NKEF antibody was used as a probe in immunoblot screening of a λgt11 cDNA library from the erythroleukemic K562 line. In screening $5\times10^5$ recombinant phage, four positive clones were identified. The cDNA inserts were subcloned into the EcoRI site of pUC18 and sequenced. The first three clones contain overlapping cDNAs from the same gene. The cDNA of the fourth clone is highly homologous to, but distinct from, that of the other three clones.

After additional subcloning and sequencing, it was found that the NKEF cDNAs fell into one of two catagodes of closely related but non-identical genes, referred to as NKEF A and B. The consensus nucleotide sequences for these NKEF cDNAs are shown in FIG. 1. The two sequences are 71% identical over their entire lengths (as calculated by GCG program "Bestfit"), with the majority of the identities in the coding region, as expected. The cap site for NKEF A is marked in the figure. To confirm the 5' end of the NKEF A mRNA, first, primer extension was performed to identify the distance to the cap site. The primer extension primer was designed to bind to nucleotides 65–94 (where the cap site=1). After this distance was determined (which contained 30 nucleotides of known cDNA sequence and 35 nucleotides of uncloned mRNA), the NKEF A 5' mRNA sequence was determined directly. The NKEF A 5' sequence shown in FIG. 1 is a consensus of data obtained from four separate sequencing experiments.

The 5' end of the NKEF B clone is that contained in the longest cloned cDNA. Likewise, the 3' ends of clones A and B are those contained in the largest cDNAs cloned. The polyadenylation signal and some polyA sequence were obtained for NKEF B. Regions in the two nucleotide sequences that are particularly homlogous are indicated.

The deduced protein sequences of NKEF A and B are set forth in SEQ ID NOS. 2 and 4, respectively. The two sequences are 75% identical over their entire lengths, which are 199 and 198 amino acids, respectively. These amino acid lengths for NKEF A and B give a predicted protein size of $22M_r$ which agrees well with the SDS polyacrylamide gel size information of $24M_r$ subunits and an approximately $48M_r$ dimer. The two proteins are 88% similar, taking into account conserved amino acid changes.

During the preliminary characterization of the NKEF protein, partial peptide sequencing was performed. The amino acid sequences reported here differ from the peptide sequences reported earlier (28) in several ways. For example, one apparently contiguous peptide is shown here to be from two different regions of the protein. One possible reason for this discrepancy is that "NKEF" appears to be a small family of 2–3 related proteins of very similar molecular weights. Consequently, the peptide sequencing was performed upon peptides derived from more than one NKEF protein.

The NKEF sequences were used to screen protein sequence databases. Several of the most significant sequence similarities are listed as follows. The deduced amino acid sequences of the mouse genes MER5 (30) and MSPZ3 (39) are closely related to the NKEF genes. MER5 is 61% identical (and 78% similar) to NKEF A and 64% identical to NKEF B. Even more striking is MSP23, which is 93% identical to NKEF A and 7.6% identical to NKEF B deduced amino acid sequences. In addition to these closely related mouse genes of unknown function, there is an interesting sequence from *Saccharomyces cerevisiae*, the thiol-specific antioxidant gene (TSA), that is 57% identical (and 70% similar) to NKEF A and 66% identical (and 75% similar) to NKEF B amino acid sequences. This is of particular interest because this yeast sequence has been demonstrated to have antioxidant activity (31, 32 and 33).

The NKEF genes are also significantly related to three bacterial genes and one amoeba gene, also of unclear function. The *Clostridium pasteuranium* (CLORUB) deduced protein sequence is 50% identical to NKEF A and 53% identical to NKEF B, the *Entamoeba histolytica* (EHISTO) deduced protein sequence (34) is 52% identical to NKEF A and 51% identical to NKEF B, and the *Helicobacter pylori* (HPYLOR) protein (35)is 43% identical to NKEF A and 48% identical to NKEF B. Lastly, tile *Salmonella typhimurium* alkyl hydroperoxide reductase C22 subunit gene (AHPC) protein sequence (19), is 34% identical to NKEF A and 30% identical to NKEF B. This high degree of sequence conservation through evolution suggests an important and basic function for NKEF.

There are three human cDNA sequences in the sequence databases sharing extensive homology with NKEF A: D11643 and D12103, the expressed sequence tags from HepG2 cells (36) and X67951, the human proliferation-associated gene, PAG (37). PAG was reported to be a gene overexpressed during cell proliferation (37). It shares 97% identity with NKEF A in its nucleotide sequence and may be identical to NKEF A. The differences in the sequences between NKEF A and PAG are probably due to polymorphism or sequencing errors in NKEF A or PAG. D11643 and D12103 appear to be fragments of cDNAs covering overlapping regions of a same gene. There are too many unidentified bases in these two sequences to indicate whether they are the products from the same gene as NKEF A. There was no functional characterization of any of the three gene products.

A computer search for potential glycosylation and phosphorylation sites in the NKEF protein sequences was performed. This yielded no glycosylation sites, but several potential phosphorylation sites were identified. NKEF A contains three potential Casein Kinase 2 (CK2) sites and six potential Protein Kinase C (PKC) sites. NKEF B contains two CK2 sites, four PKC sites as well as one cAMP-dependant phosphorylation site and one tyrosine kinase phosphorylation site. We have yet to conduct any functional studies to see which of these sites are utilized.

The mouse MER5 gene is reported to be a housekeeping-like gene (30), which suggests that it might be a member of a gene family. To investigate the degree to which NKEF might be a member of a gene family, a genomic Southern blot was made. The result of probing this blot with an NKEF A cDNA probe gives 2–3 major bands and 2–3 minor bands (at both 55° C. and 65° C. washes) while probing a duplicate blot with an NKEF B cDNA probe gives 5–6 bands (65° C. high stringency wash, and some additional minor bands at 55° C.). Some of the bands detected with the A probe crosshybridize with those detected by the B probe. This seems to indicate that there are 2–3 NKEF family members in the genome, but that there is not an extensive gene family which one would expect with a housekeeping gene like a human ribosomal protein gene which might have 11–13 bands on a genomic Southern blot (38).

Given the homology of NKEF A and B to proteins involved with oxidative stress, the transcriptional regulation of the NKEFs under conditions of oxidative stress was determined. In addition, it was determined whether native NKEF protein could protect DNA from oxidative damage.

TRANSCRIPTIONAL REGULATION OF NATURAL KILLER ENHANCING FACTOR BY OXIDATIVE STRESS

Materials and Methods
Cells

K562 cells were originally obtained from a patient diagnosed with myeloleukemia but which were later found to express erythroid characteristics. The cells were grown in RPMI1640 medium (BioWhittaker, Walkersville, Md.) supplemented with 10% Fetal Calf Serum (Gemini Bioproducts, Calabasas, Calif.), Hepes buffer (CalBiochem, San Diego, Calif.) and antibiotics (PSF; 100 µg/ml Penicillin, 100 ug/ml Streptomycin, 0.25 ug/ml Fungizone, BioWhittaker). Total RNA was isolated by the RNAzol B method (Tel-Test Inc., Friendswood, Tex.) from >1×10 cells according to the manufacturer's instructions.

Preparation of Native Human NKEF

Human NKEF was prepared by ammonium sulfate precipitation and Q-Sepharose Fast Flow colum separation as previously described. G-150 gel filtration chromatography (Pharmacia Biotech, Piscataway, N.J.) was used to further purify the protein.

DEM and Glucose Oxidase Treatment

Oxidative stress was induced in K562 cultures with DEM by dissolving 2 µl of DEM (Sigma Chemicals, St. Louis, Mo.) in 50 µl of ethanol and pipetting 8 µl of this dilution into 20 ml of K562 culture for a final DEM concentration of 100 µM. Hydrogen peroxide was generated in K562 cultures by addition of glucose oxidase enzyme (Sigma) into the glucose containing medium to a final concentration of 5 mU/ml.

Northern Blotting

Twenty micrograms of total RNA per lane was size fractionated by electrophoresis through a 1% agarose/formaldehyde gel. The RNA gel was transferred to a nylon membrane (Costar, Cambridge, Mass.; Schleicher and Schuell, Keene, N. H.; or Micron Separations, Westboro, Mass.) by downward capillary action using the Schleicher and Schuell Turbo-blotting apparatus or by vacuum transfer. Northern blots were UV crosslinked in a Stratalinker (Stratagene, La Jolla, Calif.) or baked in a vacuum oven. Hybridizations were performed using Quikhyb (Stratagene) according to the manufacturer's instructions or by utilizing the Genius System (Boehringer Mannheim, Indianapolis, Ind.) non-radioactive hybridization method according to the manufacturer's instructions. Radioactive probes were cDNAs purified from vector sequences by low melting point agarose gel electrophoresis and subsequently labelled by either nick-translation (Bethesda Research Laboratories, Gaithersberg, Md.) or random priming (Ambion, Austin, Tex.). Unincorporated nucleotides were removed by column chromatography (Qiagen, Chatsworth, Calif.; PCR Quick purification columns). Hybridized filters were exposed to X-ray film (Kodak) and the films were scanned by densitometry (Hoefer Scientific, San Francisco, Calif.). The same blots were subsequently hybridized with NKEF A, NKEF B and alpha tubulin as a control for the amount of RNA loaded onto each lane or, for in vitro differentiation, the NKEF A and B signal was compared to the stained gel 18s and 28s rRNA bands as a control.

TPA and Hero in Induction of K562 Differentiation

For TPA induction, the 5 mg/ml stock (Sigma) was diluted 1:50 in 100% ethanol and added to cells in a 1:1000 dilution such that K562 cells were exposed to 100ng/ml TPA ($1.62 \times 10^{-7}$M) for the times listed. For hemin induction, hemin (Sigma) was prepared fresh by dissolving 50 mg in 40 ml of 50 mM NaOH. The pH was adjusted to 7.4 with HCl. This solution was filtered through a 0.22 um filter then added to cells to a final concentration of 50 μM for the times listed in the figure. RNA from treated cells was prepared by the RNAzol B method (Tel-test) and subsequently northern blotted as above.

DNA Cleavage by ThioFDependent MFO System

Supercoiled pUC18 plasmid DNA was used as an indicator for detecting damage by the non-enzymatic thiol-dependent MFO system. Single strand breakage converts the plasmid from a double stranded supercoil (form I) to a relaxed double stranded open circle (form II). The reaction contained 300 ng DNA, 33 μM $FeCl_3$ and the indicated concentrations of NKEF protein. In addition, 3.3 mM dithiothreitol was added as an electron donor. The mixture was incubated at 37° C. for 3 hours then subjected to 0.8% agarose gel electrophoresis.

RESULTS

Northern blots comparing expression of NKEF A and B genes in response to exposure to DEM for various times were run. NKEF A shows a brief initial decrease followed by a strong transcriptional increase which is maximal at 24 hours. NKEF B shows a slight decrease and no further change. It should be noted that NKEF A consistently shows a much lower signal in all Northern blots compared to NKEF B. This occurred despite utilizing the same amount of probe DNA prepared by the same method for each of the two genes. This was not observed in genomic southern blot hybridization. It may indicate that K562 cells express much more NKEF B than A. This trend was observed in 5 separate experiments, many of which were performed in duplicate.

Duplicate northern blots comparing expression of NKEF A and B genes in response to exposure to hydrogen peroxide generated in the culture medium by glucose oxidase were run. The level of NKEF A does not change significantly, while NKEF B drops slightly initially then does not change further, staying at the lowest level. This lack of significant change in transcription levels was observed in two different experiments each performed in duplicate.

FIG. 2 is a graph of the average steady state mRNA levels for NKEF A and B genes after exposure to either DEM or glucose oxidase for various times. The numbers are based on densitometric scans of multiple northern blots made for each cell exposure time. At 24 hours of DEM exposure, NKEF A reaches a maximum level of 3-fold induction of steady state mRNA compared to untreated cells. For comparison between experiments, NKEF mRNA levels were normalized to alpha tubulin and the lowest levels were each set to 1 arbitrarily.

NKEF A and B are Both Transcriptionally Regulated During Differentiation of K562 Cells Northern blot analysis demonstrated a transient increase in both NKEF A and B transcription during in vitro differentiation with either TPA, which induces monocyte differentiation, or hemin, which induces erythroid differentiation. During erythroid differentiation with hemin, NKEF A is strongly up-regulated in the first 4 hours of exposure and it remains induced through 24 hours of exposure, decreasing to control unexposed levels by 48 hours. NKEF B is also strongly induced in hemin treated cells within 4 hours of treatment, but less so than A. In TPA induction of monocytic differentiation, NKEF A is again induced within 4 hours of treatment, but to a level that is less than half of the heroin level of induction. After a dip at 8 hours, NKEF A reaches its highest level at 48 hours. In contrast, NKEF B is not significantly induced due to TPA exposure, and the B level drops somewhat from 8 hours to a low at 48 hours.

Figure 3:
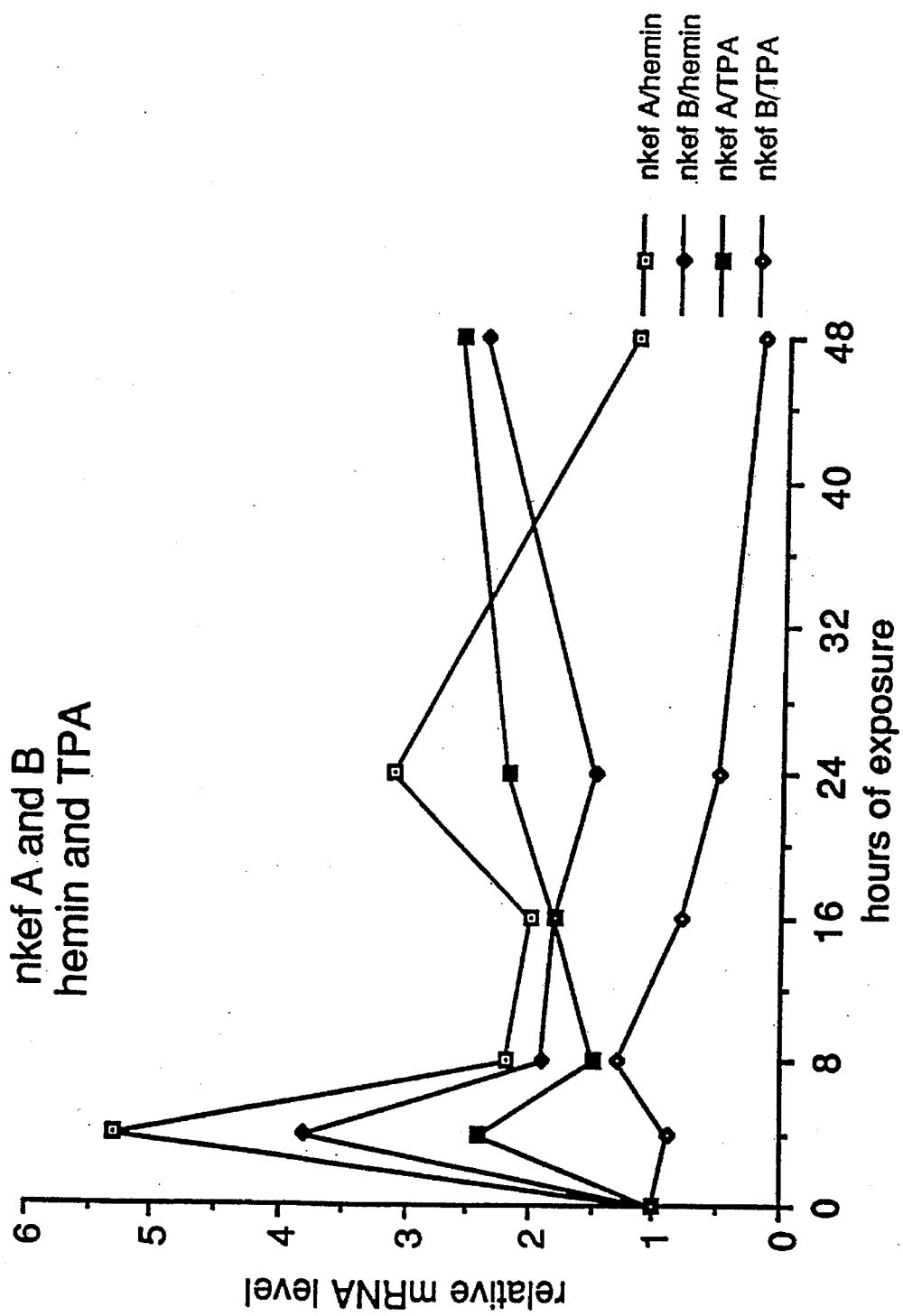
FIG. 3 is a graph depicting the relative levels of NKEF A & B mRNA after exposure of cells to either heroin or TPA.

FIG. 3 shows a graph of the relative induction of the NKEF A and B mRNAs during in vitro differentiation with either hemin or TPA. The X-ray films of the northern blots were scanned by a densitometer. This data was normalized for the amount of RNA loaded in each lane by scanning a negative of the photograph of the RNA gel before transfer and comparing NKEF A and B RNA to the 28s rRNA band. The lowest levels were set to 1 arbitrarily.

NKEF Protein Protects DNA from Damage Induced by a Thiol-Dependent MFO System

Agarose gel electrophoresis ws performed on pUC18 plasmid DNA which had been exposed to a thiol-dependent MFO system containing dithiothreitol as an electron donor. With decreasing amounts of native NKEF protein, more of the plasmid DNA is converted from the supercoiled form I to the nicked open circle form II. While most of the DNA is nicked by the MFO system in the absence of NKEF, 100 μg/ml NKEF protects most of the plasmid from oxidative damage. When only 6.25 μg/ml of the native NKEF is present in the assay, most of the plasmid becomes nicked. To determine whether protection of DNA by NKEF was due to contamination by other known antioxidants, we tested each native NKEF preparation for the activity of catalase and superoxide dismutase (data not shown) and found there to be no such contamination.

Both NKEF A and B share extensive identity with a yeast protein termed thiol-specific antioxidant (TSA) (2). TSA protects yeast from oxidative insults. An in vitro assay system for TSA takes advantage of its ability to protect glutamine synthetase and other enzymes from inactivation by reactive oxygen intermediates (ROI) and/or thiol radicals generated in the mixed metal-thiol oxidation system. It is believed that ROI and thiol radicals are generated in the system by the following reactions: [1] $R\text{-}SH+Fe^{3+} \rightarrow R\text{-}S^{\cdot}+H^{+}+Fe^{2+}$ [2] $Fe^{2+}+O_2 \rightarrow Fe^{3+}O_2^{-\cdot}$ [3] $2\ O_2^{-\cdot}+2\ H^{+} \rightarrow H_2O_2+O_2$ [4] $R\text{-}S^{\cdot}+R\text{-}SH \rightarrow R\text{-}S\text{-}S\text{-}R^{-\cdot}+H^{+}$ [5] $R\text{-}S\text{-}S\text{-}R^{-\cdot}+H_2O_2 \rightarrow R\text{-}S\text{-}S\text{-}R+OH^{-}+OH^{\cdot}$. This chain reaction can be blocked by cation chelators like EDTA or by hydrogen peroxide scavengers like catalase. Indeed, both EDTA and catalase protect glutamine synthetase from inactivation in the system. Unlike catalase, TSA does not directly scavenge hydrogen peroxide. Therefore, TSA represents a new class of natural antioxidants in protecting cells from oxidative insults. Because of the significant shared identity between TSA and NKEF, we investigated the antioxidant activity of NKEF.

NATURAL KILLER ENHANCING FACTOR IS A MAJOR ANTIOXIDANT IN HUMAN RED BLOOD CELLS

Materials and Methods

Preparation of RBCs, cytosol and NKEF: RBCs from normal donors and RBC cytosol were prepared as previously described (28). NKEF was highly purified by ammonium sulfate precipitation and Q-Sepharose Fast Flow column as before (28). All protein samples were dialyzed in 50 μM of imidazole HCl buffer (pH 7.0) before testing.

Depletion of NKEF and SDS-PA GE analysis: Rabbit anti-human NKEF antibodies were generated as previously described (28). One ml of the antiserum was bound to 5 ml of Pharmacia (Alameda, Calif.) protein G Sepharose 4 Fast Flow beads to create a NKEF-specific antibody column. Four mg of RBC cytosol proteins in 1.5 ml of 20 mM sodium phosphate buffer (pH 7.0) were loaded onto the anti-NKEF antibody column, and the proteins not bound to the antibodies were washed off the column with the same buffer. SDS-PAGE analysis of proteins was performed under reducing condition and the gels were stained by Coomassie Blue as reported (28).

Antioxidant activity of NKEF and mixed thiokmetal oxidation of glutamine synthetase: Antioxidant activity of NKEF was measured by its ability to protect glutamine synthetase from inactivation by mixed metal-thiol oxidation. Glutamine synthetase function was indicated by its glutamyltransferase activity (31,33), performed in microwells. NKEF protein at indicated concentration was mixed with glutamine synthetase (1.5 units/ml), 33 μM of $FeCl_3$, and 27 mM of 2-mercaptoethanol as thiol reagent in a total volume of 150 μl of 50 mM imidazole HCl buffer (pH 7.0). After 15 minutes incubation at 37° C., 50 μl of glutamine synthetase substrate containing 150 mM glutamine, 400 μM ADP, 20 mM potassium arsonate, 20 mM of neutralized $NH_2OH$ HCl, and 400 μM $MnCl_2$ in imidazole buffer was added. Following 30 more mins of incubation, 50 μl of stop solution containing 55 g/l of $FeCl_3$, 20 g/l of trichloric acid, and 105 ml/l of HCl was added. The plate was read with an ELISA plate reader at 550 nm wave length.

Reagents: Unless indicated otherwise, the chemicals were purchased from Sigma Chemicals (St. Louis, Mo.).

RESULTS

NKEF is an abundant protein in RBC: In SDS-PAGE analysis, we observed that the protein with an apparent molecular mass of 22–24 kDa, same as that of NKEF, was the third or fourth most abundant protein band in the whole RBC cytosol. To further identify this abundant protein, we passed RBC cytosol through the antibody column specific for human NKEF. The 22–24 kDa band is mostly depleted by the anti-NKEF column, further indicating that this abundant protein in RBC cytosol is NKEF.

Antioxidant function of NKEF: Both NKEF-A and B share extensive homology with the yeast TSA. Using the Bestfit program of the University of Wisconsin's Genetics Computer Group software, we found that TSA shares 57% identity and 70% similarity with NKEF-A, and 66% identity and 75% similarity with NKEF-B at the amino acid level. It is not yet known whether the native NKEF from RBC cytosol is the product of NKEF-A or B, or a mixture of both.

Since NKEF and the yeast TSA share extensive homology with each other, we tested for the antioxidant activity of NKEF. Treatment with the mixed metal-thiol oxidative system inactivates most of the glutamyltransferase activity of glutamine synthetase (31). However, in the presence of NKEF, glutamine synthetase is protected from the oxidative inactivation. The protective activity of NKEF is dose-dependent. Higher concentrations of NKEF provide greater protection of glutamine synthetase from oxidative damage. Similar dose dependent antioxidant function of NKEF was observed in five separate experiments. NKEF itself has no glutamine synthetase activity. Like NKEF, the hydrogen peroxide scavenger catalase also protects glutamine synthetase from inactivation by mixed metal-thiol oxidation. However, on the basis of unit protein weight, NKEF is at least twice as effective as catalase in protecting glutamine synthetase.

We also tested for the catalase-like activity of NKEF.

The results show that NKEF cannot directly scavenge hydrogen peroxide. In contrast, catalase at the same concentration rapidly eliminates hydrogen peroxide. These results were repeated in three other similar experiments. Therefore, NKEF protects enzymes from mixed metal-thiol oxidative inactivation via a mechanism distinct from direct elimination of hydrogen peroxide in the system.

Having thus described the exemplary embodiments of the present invention, it should be noted by those skilled in the art that the within disclosures are exemplary only and that various alternatives, adaptations and modifications may be made within the scope of the present invention. Accordingly, the present invention is not limited to the specific embodiments as illustrated herein, but is only limited by the following claims.

BIBLIOGRAPHY

1. Trinchieri, G., *Adv. Immunol.*, 47:187–376, 1989.
2. Whiteside, T. L. and Herberman, R. B., *Clin. Immunol. Immunother.*, 53:1–23, 1989.
3. Storkus, W. J. & Dawson, J. R., *Critical Rev. Immunol.*, 10:393–416, 1991.
4. Golub, S. H., D'Amore, P. and Rainey, M., "Systemic Administration of Human Leukocyte Interferon to Melanoma Patients. II. Cellular Events Associated With Changes in NK Cytotoxicity," *J. Nat'l. Cancer Inst.*, 68:711–717, 1982.
5. Ebina, N., Gallardo, D., Shau, H., and Golub, S. H., *Br. J. Cancer*, 62:619–623.
6. Swisher, S. G., Economou, J. S., Holmes, E. C., and Golub, S. H., *Cell Immunol.*, 128:450–461, 1991.
7. Iho, S., Shau, H., and Golub, S. H. *Cell. Immunol.*, 135:66–67.
8. Shau, H. and Golub, S. H., *Cell. Immunol.*, 116:60–72, 1989.
9. Plunkett, M. L., Sanders, M. E., Slevaraj, P., Dustin, M. L., and Springer, T. A. *J. Exp. Med.*, 165:664–676, 1987.
10. Perussia, B., Starr, S., Abraham, S., Fanning, V., and Trinchieri, G., *J. Immunol.*, 130:2133–2141, 1983.
11. Euhus, D. M., Gupta, R. K., and Morton, D. L., *Cancer Immunol. Immunother.*, 32:214–220, 1990.
12. Yamamoto, T., Matsui, S., Natori, S., and Obinata, M., *Gene* 80:337–343, 1989.
13. Pross, H. F., Baines, M. G., Rubin, P., Shrugge, P., and Patterson, M. S. *J. Clin. Immunol.* 1:51–71, 1981.
14. Sambrook, J., Fritsch, E. F., and Maniatis, T., *Molecular Cloning: a Laboratory Manual*, Cold Spring Harbor Laboratory Press, Cold Spring Harbor, N.Y., 1989.
15. Young, R. A., and Davis, R. W., "Efficient isolation of genes using antibody probes," *Proc. Natl. Acad. Sci. USA*, 80:1194–1198 (1985).
16. Chang et al., *Nature*, 275:615 (1976).
17. Goeddel et al., *Nature*, 281:544 (1979).
18. Goeddel, D., *Nucleic Acids Res.*, 8:4057 (1980)
19. de Boer, H., *PNAS (USA)*, 80:21–25 (1983).

20. Siebenlist et al., *Cell,* 2 (1980).
21. Stinchomb et al., *Nature,* 282:39 (1979).
22. Kingsman et al., *Gene,* 7:141 (1979).
23. Tschemper et al., *Gene,* 10:157 (1989).
24. Jones, *Genetics,* 85:12 (1977).
25. Fiers et al., *Nature,* 273:113 (1978).
26. Greenaway, P. J. et al., *Gene,* 18:355–360 (1982).
27. Anderson, L. C.: "Induction of Erythroid Differentiation in the Human Leukemia Cell Line K562" *Nature* 278:364–365 (1979).
28. Shau, et al.: "Regulation of Natural Killer Cell Function by Non-lymphoid Cells" In: *Natural Killer Cells: Their Definition, Functions, Lineage and Regulation*, E. Lotzova, editor pp. 235–349 (1993).
29. Geliebter, J.: "Dideoxy Sequencing of RNA and Uncloned cDNA" *BRL Focus* 9:5–8 (1987).
30. Yamamato, et al.: "Cloning of a housekeeping-type gene (MER 5) Preferentially Expressed in Murine Erythroleukemia Cells" *Gene* 80: 337–343 (1989).
31. Kim, et al.: "The Isolation and Purification of a Specific Protector Protein Which Inhibits Enzyme Inactivation by a thiol/Fe(III)/$O_2$ Mixed Function Oxidation system." *J. Biol. Chem* 263:4704–4711 (1988).
32. Kim, et al.: "Induction of an Antioxidant Protein of *Saccharomyces cerevisiae* by $O_2$, $Fe^{3/}$, of 2-Mercaptoetherol." *Proc. Natl. Acad. Sci. USA*, 86:6018–6022 (1989).
33. Chau, et al.: "Cloning Sequencing and Mutation of Thiol-Specific Antioxidant Gene of *Saccharomyces cerevisae*" *J. Biol. Chem.* 268: 16815–16821 (1993).
34. Reed, et al.: "Molecular and Cellular Characterization of the 29-kilodalton Peripheral Membrane Protein of *Entamoeba histolytic*: Differentiation Between Pathogenic and Nonpathogenic Isolates" *Infec. Immun.* 60:542–549 (1992).
O'Toole et al.: "Isolation and Biochemical and Molecular Analysis of Species-Specific Protein Antigen From the Gastric Pathogen *Helicobacter pylori*" *J. Bacteriol.* 173: 505–513 (1991).
36. Okubo et al.: "Large Scale cDNA Sequencing For Analysis of Quantitative and Qualitative Aspects of Gene Expression" *Nature Genetics* 2: 173–179 (1992).
37. Prosperi et al.: "A Human cDNA Corresponding to a Gene Overexpressed During Cell Proliferation Encodes a Product Sharing Homology With Amoebic and Bacterial Proteins." *J. Biol. Chem* 268: 11050–11056 (1993).
38. Butterfield, L. H.: "Characterization of the Human Homologue of Rate Ribosomal Protein L26 and its Regulation in HL60 Human Promyelocytic Leukemia Cells During In Vitro DMSO Differentiation to Neutrophils" Ph. D. Dissertation (1993).
39. Ishi et al.: "Cloning and Charracterization of a 23 kDa Stress-Induced Mouse peritoneal Macrophage Protein. *J. Biol. Chem* 268: 18633–636 (1993)

---

What is claimed is:

1. A recombinant DNA molecule comprising a DNA sequence encoding natural killer cell enhancing factor A as defined in SEQ ID NO: 2.

2. A recombinant DNA molecule comprising a DNA sequence encoding natural killer cell enhancing factor B as defined in SEQ ID NO: 4.

\* \* \* \* \*